(12) United States Patent
Miyazaki (10) Patent No.: US 8,792,610 B2
(45) Date of Patent: Jul. 29, 2014

(54) METHOD AND APPARATUS FOR X-RAY CT IMAGING

(75) Inventor: Hiroaki Miyazaki, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 471 days.

(21) Appl. No.: 13/081,022

(22) Filed: Apr. 6, 2011

(65) Prior Publication Data

US 2011/0243298 A1 Oct. 6, 2011

(30) Foreign Application Priority Data

Apr. 6, 2010 (JP) .................................. 2010-088075
Apr. 6, 2011 (JP) .................................. 2011-84129

(51) Int. Cl.
*G01N 23/083* (2006.01)
*H05G 1/64* (2006.01)
*H01J 35/02* (2006.01)

(52) U.S. Cl.
USPC ............... 378/15; 378/12; 378/137; 378/210; 378/901

(58) Field of Classification Search
USPC ........... 378/4–20, 62, 91, 125, 135–137, 145, 378/204, 210, 901
See application file for complete search history.

(56) References Cited

U.S. PATENT DOCUMENTS

| 5,625,661 | A | * | 4/1997 | Oikawa ........................... 378/15 |
| 7,769,129 | B2 | | 8/2010 | Hein et al. |
| 2009/0110257 | A1 | | 4/2009 | Hein et al. |

FOREIGN PATENT DOCUMENTS

JP 2010-035812 2/2010

OTHER PUBLICATIONS

T. G. Flohr et al. "Image reconstruction and image quality evaluation for a 64-slice CT Scanner with z-flying focal spot." Medical Physics 32 (8), Aug. 2005, p. 2536-2547.

* cited by examiner

*Primary Examiner* — Anastasia Midkiff
(74) *Attorney, Agent, or Firm* — Oblon, Spivak, McClelland, Maier & Neustadt, L.L.P.

(57) ABSTRACT

An apparatus for X-ray CT imaging including an X-ray irradiation unit configured to irradiate an X-ray toward a subject, an X-ray detector having a plurality of X-ray detection elements along a channel direction and a row direction, a couch on which the subject can be arranged, a rotation unit on which the X-ray irradiation unit and the X-ray detector are oppositely disposed and rotate around the couch, a controller configured to execute a helical scan while fluctuating an X-ray focal spot along a body axis direction of the subject by controlling the X-ray irradiation unit, and an image processing unit configured to generate a reconstructed image based on data acquired by the helical scan, wherein the controller is further configured to set a magnitude of fluctuation of the X-ray focal spot so that data acquisition loci of the helical scan do not overlap each other.

20 Claims, 12 Drawing Sheets

METHOD AND APPARATUS FOR X-RAY CT IMAGING

CROSS-REFERENCE TO RELATED APPLICATIONS

This application is based upon and claims the benefit of priority from Japanese Patent Application No. 2010-88075, filed Apr. 6, 2010, and Japanese Patent Application No. 2011-84129, filed Apr. 6, 2011, the entire contents of which are incorporated herein by reference.

FIELD

Embodiments described herein relate generally to a method and an apparatus for X-ray CT (Computed Tomography) imaging, and more particularly to techniques for helical scan adapting flying focal spot.

BACKGROUND

An X-ray CT apparatus has an X-ray tube and an X-ray detector that are oppositely provided across the subject. The X-ray detector includes a plurality of channels of X-ray detection elements along the channel direction, which is perpendicular to the longitudinal direction of the couch (body axis direction).

Meanwhile, a multi-slice X-ray CT apparatus has a plurality of rows of X-ray detector elements not only along the channel direction, but also along the body axis direction of the subject. The X-ray detector of the multi-slice X-ray CT apparatus is configured as a two-dimensional detector for X-ray CT having M channels by N rows of X-ray detector elements.

The multi-slice X-ray CT apparatus executes a conventional scan using a FFS (Flying Focal Spot) method that enables the X-ray focal spot to fluctuate along the z-axis direction (body axis direction) around the original focal spot. Hereinafter, the FFS method for fluctuating the X-ray focal spot along the z-axis direction is referred to as the z-FFS method.

In the case of a conventional scan of a multi-slice X-ray CT apparatus using the z-FFS method, the focal spot is changed for each view. For example, the position of the focal spot of an odd-number-turn view is $+\sigma$, while the position of the focal spot of an even-number-turn view is $-\sigma$. The conventional scan causes the that sampling pitch of the data to be half, compared to the conventional scan without the z-FFS method. The flying focal spots $\pm\sigma$ are shown by following expression.

$$\pm\sigma = \pm\frac{d \cdot SOD}{4 \cdot (SDD - SOD)}$$

Here, the SOD (source to object distance) is defined as the distance between the focal spot of the X-ray tube and the rotational center (isocenter), the SDD (source to detector distance) is defined as the distance between the focal spot of the X-ray and the center of the X-ray detector, and d is defined as a pitch of the X-ray detector elements.

DETAILED DESCRIPTION

An apparatus and a method for X-ray CT imaging according to an exemplary embodiment will be described referring to the accompanying drawings.

Note that the X-ray CT apparatus according to one embodiment has various types including a rotate/rotate type having an X-ray tube and an X-ray detector in pairs as an integrated structure rotating around an object, and a stationary/rotate type having plural detection elements arrayed to form a ring-like shape to allow only the X-ray tube to rotate around the object. Embodiments disclosed herein are applicable to any type of CT system. However, in the following discussion, the rotate/rotate type will be assumed.

A mechanism for converting the incident X-ray into a charge has mainly two forms, i.e., (1) an indirect conversion for converting an X-ray into light through a phosphor such as a scintillator, and further converting the light into the charge through a photoelectric conversion element such as a photodiode, and (2) a direct conversion that uses an electron-hole pair generated in a semiconductor by the X-ray to move to a corresponding electrode, that is, a photoconductive phenomenon.

Recently, an X-ray CT apparatus of the multi-tube type having plural pairs of an X-ray tube and an X-ray detector installed in a rotary ring has been increasingly put into practical use, and peripheral technology has been developed as well. One embodiment is applicable to both the X-ray CT apparatus of the known single-tube type and that of the multi-tube type. Herein, the X-ray CT apparatus of the single-tube type will be described.

Figure 1:
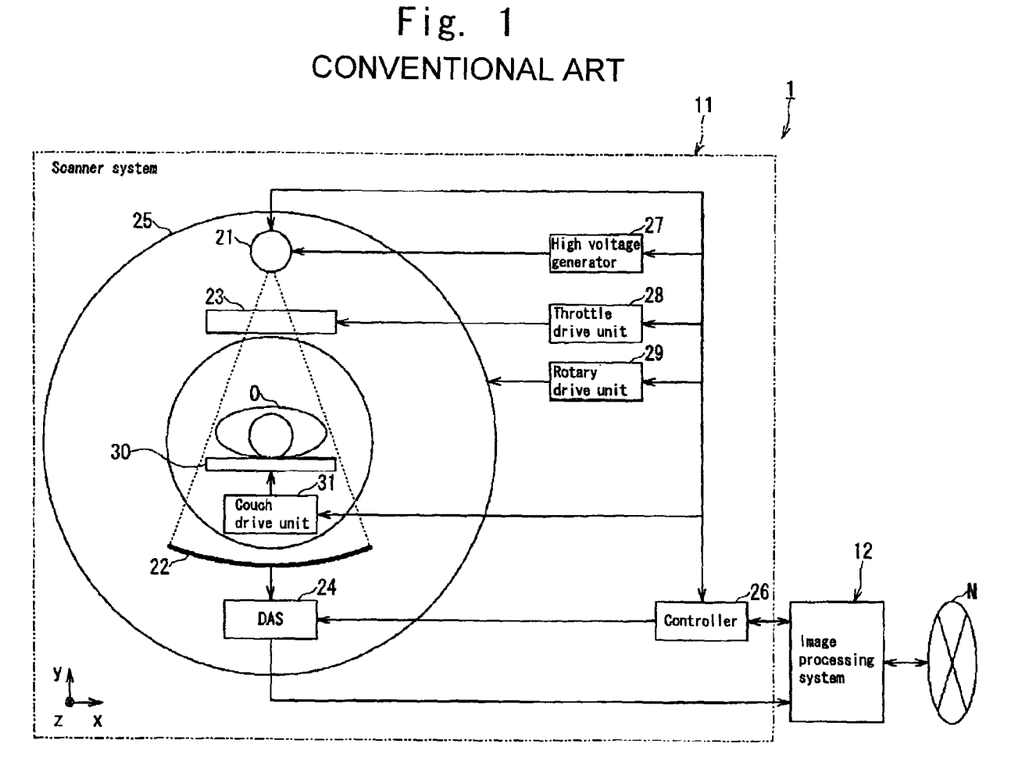
FIG. 1 is a schematic diagram showing a hardware structure which represents an X-ray CT apparatus according to one embodiment.

FIG. 1 is a schematic diagram showing a hardware structure which represents an X-ray CT apparatus according to one embodiment.

FIG. 1 shows a CT apparatus 1 according to the present exemplary embodiment. The X-ray CT apparatus 1 is includes a scanner system 11 and a image processing system 12. The scanner system 11 of the X-ray CT apparatus 1 is normally set in an inspection room and is structured to generate projection data of a patient (object) O. Meanwhile, the image processing unit 12 is normally provided in a control room neighboring the inspection room and executes generation/display of reconstruction image data based on the projection data.

The scanner system 11 of the X-ray CT apparatus 1 has an X-ray tube 21, an X-ray detector 22, a throttle 23, a DAS (data acquisition system) 24, a rotation unit 25, a controller 26, a high voltage generator 27, a throttle drive unit 28, a rotary drive unit 29, a couch 30, and a couch drive unit 31.

The X-ray tube 21 generates an X-ray by collision of an electron beam to a metal target in accordance with a tube voltage supplied from the high voltage generator 27, and irradiates a cone-beam or fan-beam X-ray toward the X-ray detector 22. The controller 26 causes the necessary electric power to be supplied to the X-ray tube 21 via the high voltage generator. The controller 26 also controls fluctuation along the z-axis direction of the z-FFS method. The magnitude of the fluctuation can be defined as $D=2\sigma$.

The X-ray detector 22 is a 2D array type (or multi-slicing type) having plural X-ray detection elements in a matrix (channel direction and row or slice direction). The X-ray detection elements of the X-ray detector detect X-rays irradiated from the X-ray tube 21.

The throttle 23 shown in FIG. 1 is controlled by the throttle drive unit 28 to adjust the range of the X-ray along the slice direction. That is, an opening of the throttle 23 is adjusted by the throttle drive unit 28 so as to change the X-ray exposure range in the slice direction.

The DAS 24 amplifies the signal output from the X-ray detector 22 for each channel, and further converts the signal into a digital signal. The converted raw data are supplied to the external image processing system 12.

The X-ray tube 21, the X-ray detector 22, the throttle 23, and the DAS 24 are disposed on the rotation unit 25 of a gantry (not shown) of the scanner system 11. The rotation unit 25 is structured to allow the oppositely disposed X-ray tube 21 and the X-ray detector 22 to rotate as a pair around the subject O. Note that a direction in parallel with a rotation center axis of the rotation unit 25 is designated as a z-axis direction (row direction). A plane orthogonal to the z-axis direction is defined by an x-axis direction and a y-axis direction.

The controller 26 includes basic hardware such as a CPU (central processing unit) and a memory. The controller 26 controls the X-ray tube 21, the DAS 24, the high voltage generator 27, the throttle drive unit 28, the rotary drive unit 29, the couch drive unit 31, etc. Based on a control signal input from the image processing system 12, the controller 26 causes the execution of a scan, such as a helical scan, using the z-FFS method. In the z-FFS method, the flying focal spots ±σ are defined as the positions of the focal spot that changes for each view.

The high voltage generator 27 supplies the power required for the X-ray exposure to the X-ray tube 21 under the control of the controller 26. The high voltage generator 27 has a high voltage transformer (not shown), a filament heating converter (not shown), a rectifier (not shown), and a high voltage switching unit (not shown).

The throttle drive unit 28 is controlled by the controller 26 to adjust the X-ray exposure range of the throttle 23 in the row direction.

The rotary drive unit 29 is controlled by the controller 26 to rotate the rotation unit 25 around a hollow portion continuously, while maintaining the positional relationship of the rotation unit 25.

The subject O lies on the couch 30.

The couch drive unit 31 is controlled by the controller 26 to move the couch 30 along the row direction. An opening is formed at a center of the rotation unit 25 into which the subject O lying on the couch 30 is moved.

The image processing system 12 of the X-ray CT apparatus 1 includes a computer, and is capable of inter-communicating with a network N, such as LAN, as the core system in a hospital. The image processing system 12 includes basic hardware such as a CPU, a memory, a HD (hard disk), an input device, and a display device 46, each of which is not shown.

The image processing system 12 generates the projection data by subjecting the raw data input from the DAS 24 of the scanner system 11 to pre-processing (e.g., a logarithmic conversion process and a correction process such as a sensitivity correction). The image processing system 12 also eliminates the scattered ray based on the pre-processed projection data. Specifically, the projection data subjected to the scattered ray correction, or the scattered ray estimated based on the value size of the adjacent projection data, will be subtracted from the target projection data so as to execute the scattered ray correction. The image processing system 12 generates a reconstructed image based on the corrected projection data.

Figure 2:
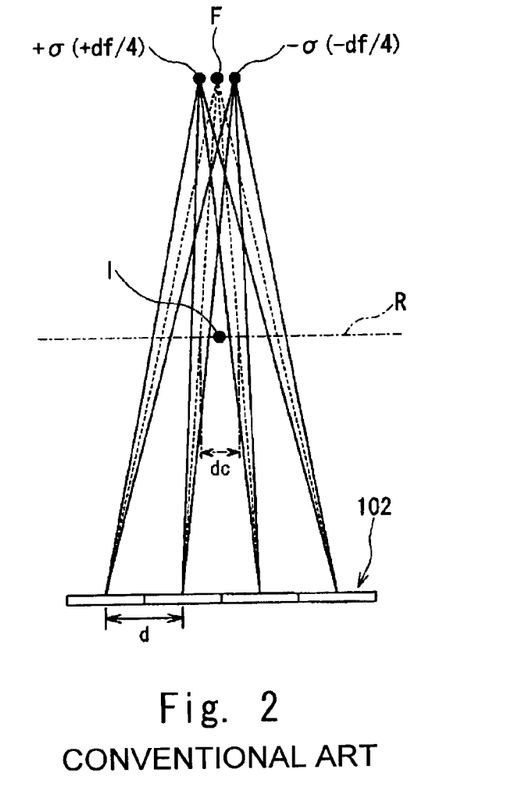
FIG. 2 is a schematic diagram showing an X-ray path in the case of a conventional scan using the z-FFS method applying the conventional flying focal spot.

FIG. 2 is a schematic diagram showing an X-ray path in the case of a conventional scan using the z-FFS method applying the conventional flying focal spot.

FIG. 2 shows the X-ray focal spot F when the z-FFS method is not applied, and flying focal spots ±σ when the z-FFS method that causes fluctuation of the X-ray focal spot along the z-axis is applied. FIG. 2 also shows an X-ray detector 102 having 4 rows of X-ray detection elements along the slice direction, rotation center R, and X-ray paths (position of projection data) connecting each of the focal spots F ±σ and the centers of each of the X-ray detector elements, wherein d is the pitch of the X-ray detector elements. Meanwhile, the X-ray path connecting focal spot F is shown by a dashed line, while the X-ray paths connecting each of the flying focal spots ±σ is shown by a solid line.

The conventional flying focal spots ±σ can be shown by expression (1) below. Here, the SOD (source to object distance) is defined as the distance between the focal spot of the X-ray tube and the rotation center (isocenter I), the SDD (source to detector distance) is defined as the distance between the focal spot of the X-ray tube and the center of the X-ray detector 102, and the dc (projected detector pitch) is defined as a pitch-projected pitch of the X-ray detector elements 22 to the rotation center R.

$$\pm \sigma = \pm \frac{dc \cdot SDD}{4 \cdot (SDD - SOD)} \quad (1)$$

Meanwhile, the relation of the pitch dc and pitch d (the pitch between the X-ray detector elements) can be expressed by the following expression (2)

$$dc = \frac{SOD}{SDD} \cdot d \quad (2)$$

Conventional flying focal spots ±σ can be expressed by the following expression (3), based on above mentioned expression (1) and expression (2).

$$\pm\sigma = \pm\frac{d \cdot SOD}{4 \cdot (SDD - SOD)} = \pm\frac{df}{4} \quad (3)$$

$$\text{Here, } f = \frac{SOD}{SDD - SOD}.$$

In FIG. 2, the distance between solid lines on the rotation center R is ½ of the distance between the dashed lines. That means that the X-ray paths using the z-FFS method in a conventional scan enables half the sampling pitch, compared to X-ray paths not using the z-FFS method in a conventional scan.

Next, the sampling pitch of a helical scan is explained. First, the helical pitch of a helical scan is set using a projected detector pitch (projected pitch of the X-ray detector elements 22 to the rotation center R indicated as dc in FIG. 2) as a unit. If the helical pitch is equal to an integral multiple of the projected detector pitch dc and only direct data is considered, the sampling pitch of the helical scan is not different from the projected detector pitch. Therefore, generally, the helical pitch is set as a half-integer multiple of the projected detector pitch (e.g., 2.5 of the projected detector pitch), for improving sampling pitch. In this case, since direct data of different rotation cycles do not overlap each other, regions where the sampling pitch is dc/2 appear. In other words, applying 2.5 of the projected detector pitch to the helical pitch results in a high resolution helical scan.

Figure 3:
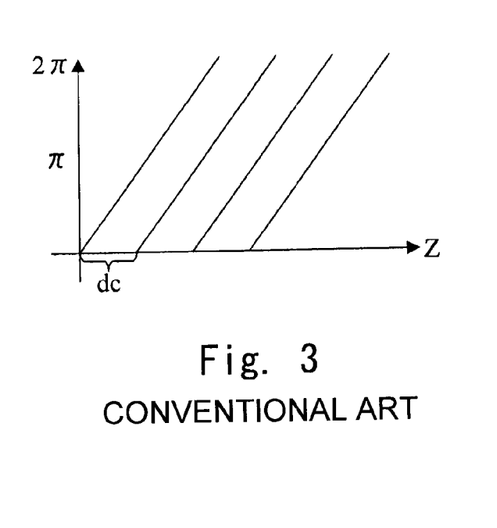
FIG. 3 is a schematic diagram showing the loci of acquisition data of the 4-row X-ray detector elements for one cycle using a 2.5 dc helical pitch.

FIG. 3 is a schematic diagram showing the loci of acquisition data of the 4-row X-ray detector elements for one cycle using a 2.5 dc helical pitch. In FIG. 3, the horizontal axis is along the z direction of acquisition data and the longitudinal axis is along the rotation angle of acquisition data. When the above-described scan is repeated, another 2.5 dc shifted acquisition loci shown in the FIG. 3 is superimposed on the acquisition loci.

Figure 4:
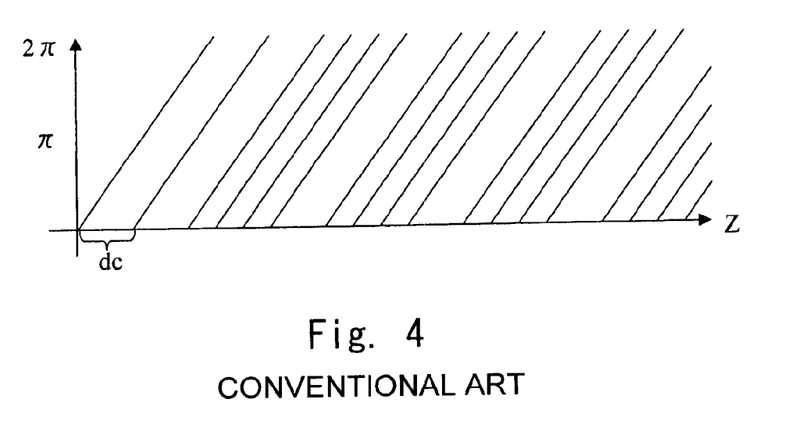
FIG. 4 is a schematic diagram showing the loci of acquisition data of the 4-row X-ray detector elements for a plurality of cycles.

FIG. 4 is a schematic diagram showing the loci of acquisition data of the 4-row X-ray detector elements for a plurality of cycles. As indicated in FIG. 4, the distances between each acquisition loci is either ½ dc or dc, appearing in a regular manner.

Figure 5:
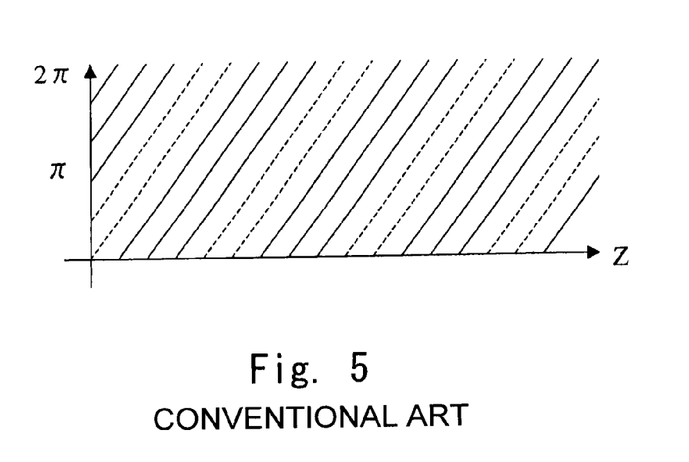
FIG. 5 is a schematic diagram showing the loci of acquisition data of the 4-row X-ray detector elements for one cycle using a 2.5 dc helical pitch and the z-FFS method adapting the conventional flying focal spot.

FIG. 5 is a schematic diagram showing the loci of acquisition data of the 4-row X-ray detector elements for one cycle using 2.5 dc helical pitch and the z-FFS method adapting the conventional flying focal spot. In this figure, for simplification, only the region where the data acquisition loci appear in a regular manner is shown, without regions where the data acquisition starts and ends. Hereinafter, if any figure does not show data loci of a start or end period like FIG. 5, the figure only shows the region where the data acquisition loci appear in a regular manner.

If a helical scan is executed using the conventional flying focal spots ±σ expressed by the expression (3) adapted to the z-FFS method and a 2.5 dc helical pitch, with neighboring two data acquisition loci distance being ½ dc, one locus of flying focal spot +σ and the other locus of flying focal spot −σ overlap each other. FIG. 5 shows the overlapped loci as a solid line and the non-overlapped loci as a dashed line. When a helical scan is executed using the conventional flying focal spots ±σ expressed by the expression (3) adapted to z-FFS method and a 2.5 dc helical pitch, the sampling pitch is not so much different from when a helical scan not using the z-FFS method (as shown in FIG. 4) and there is less effect of the z-FFS method.

Next, the X-ray CT apparatus 1 of the present exemplary embodiment that enables high-density data acquisitions when a helical scan is executed using the z-FFS method will be described.

Figure 6:
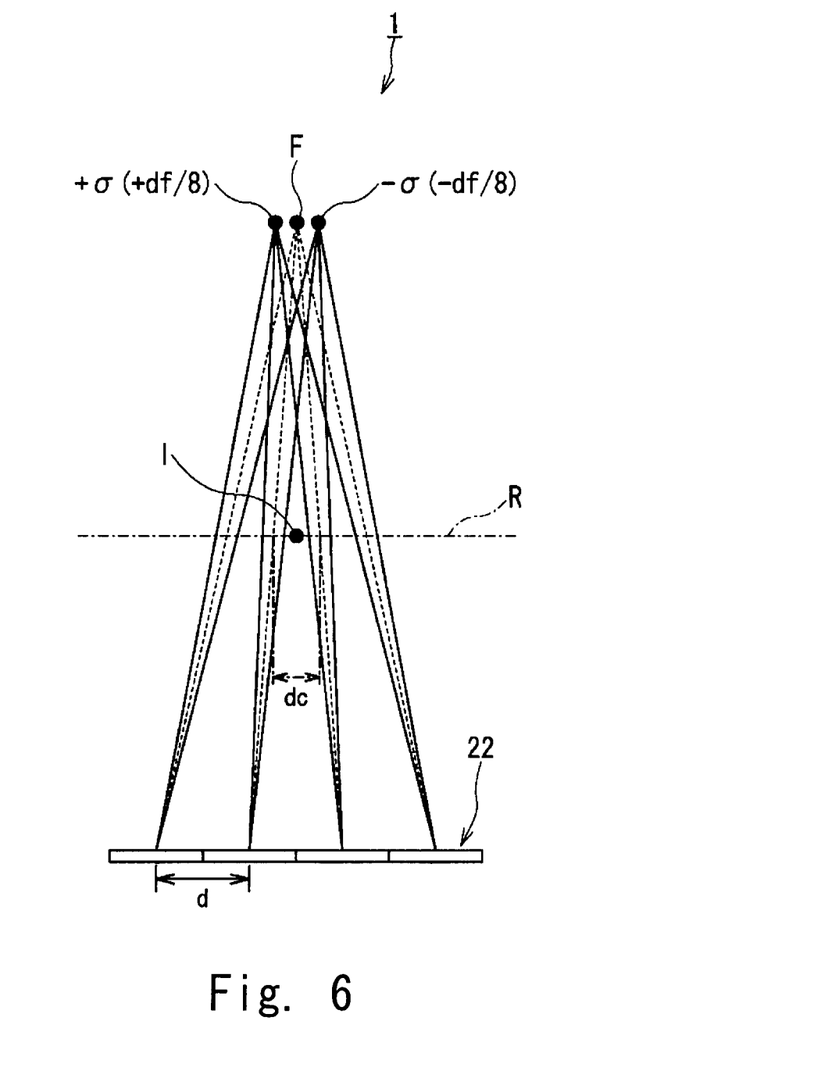
FIG. 6 is a schematic diagram showing the X-ray path using the z-FFS method of one embodiment.

FIG. 6 shows the X-ray focal spot F when the z-FFS method is not applied, and the flying focal spots ±σ when the z-FFS method of the present exemplary embodiment that cause fluctuation of the X-ray focal spot along the z-axis is applied. FIG. 6 also shows an X-ray detector 22 having 4 rows of X-ray detection elements along the slice direction, rotation center R, and X-ray paths (position of projection data) connecting each of the focal spots F ±σ and the center of each of the X-ray detector elements, wherein d is the pitch of the X-ray detector elements. Meanwhile, the X-ray path connecting focal spot F is shown by a dashed line, while the X-ray paths connecting each of flying focal spots ±σ is shown by a solid line.

Figure 7:
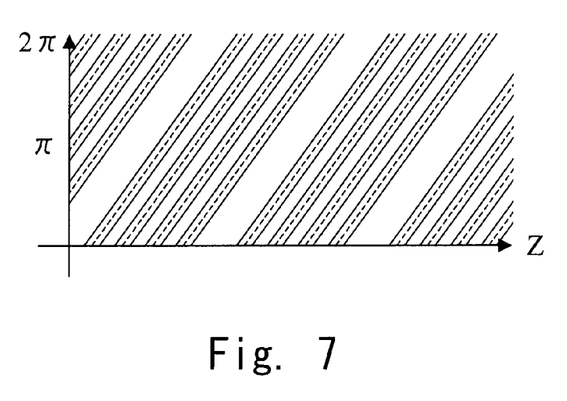
FIG. 7 is a schematic diagram showing the loci of acquisition data of helical scans using the z-FFS method adapting the flying focal spot in one embodiment.

FIG. 7 is a schematic diagram showing the loci of acquisition data of helical scans using the z-FFS method adapting flying focal spots in one embodiment. In FIG. 7, solid lines show data acquisition loci. Dashed lines show loci acquired by a scan not using the z-FFS method for reference. FIG. 7 shows data acquisition loci when the flying focal spots ±σ are ±df/8. Such a flying focal spot setting causes the data acquisition loci to not overlap each other and to have a higher density compared to the case of not using z-FFS.

As FIG. 5 shows, when the helical scan is executed using the z-FFS method adapting ±df/4 as flying focal spots ±σ, since the loci of the flying focal spot +σ and the loci of the flying focal spot −σ overlap each other, the sampling pitch is not so much different from the case of not using z-FFS. However, in the X-ray CT apparatus of the present exemplary embodiment, the flying focal spots ±σ are set to ±df/8 so that the loci do not overlap and have a higher density than when the flying focal spots ±σ are ±df/4.

In addition, this exemplary embodiment is not limited to the case in which the helical pitch is 2.5 dc, as explained above. If the helical pitch is (an integer n+0.5) dc (e.g., 1.5 dc, 3.5 dc, etc.), there can exist regions where the distances between each acquisition loci is ½ dc. In such cases, setting the flying focal spots ±σ to ±df/8 causes the loci to not overlap each other, as with the case of the helical pitch being 2.5 dc.

Furthermore, this exemplary embodiment should not be limited to the case in which the flying focal spots ±σ are ±df/8, as explained above. The flying focal spots ±σ may be set to other values so that the loci do not overlap each other. Therefore, the flying focal spots ±σ may be at least ±σ<±df/4.

First Modified Embodiment

Next, a first modified embodiment is described below. In the above embodiment, direct data is used. However, in the first modified embodiment, complementary data is also used.

Figure 8:
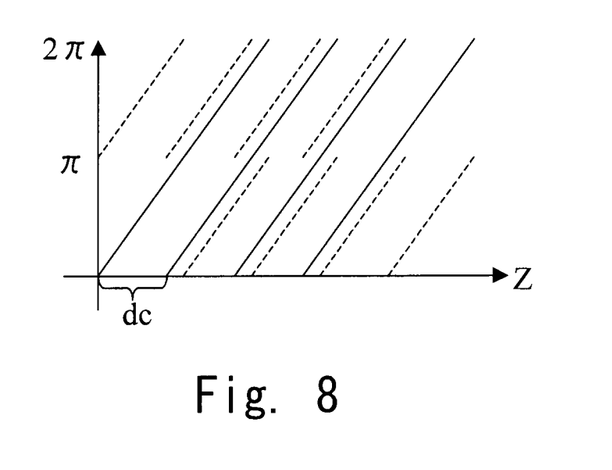
FIG. 8 is a schematic diagram showing the loci of acquisition data including direct data and complementally data of the 4-row X-ray detector elements for one cycle using a 2.5 dc helical pitch.

First of all, the data loci when complementary data is used is described. FIG. 8 is a schematic diagram showing the loci of acquisition data of the 4-row X-ray detector elements for one cycle using a 2.5 dc helical pitch. Solid lines indicate direct data and dashed lines indicate complementary data. Complementary data positions are at π shifted positions along the rotational direction from direct data. When the above scan is repeated, another 2.5 dc shifted acquisition loci shown in the FIG. 8 is superimposed on the acquisition loci.

Figure 9:
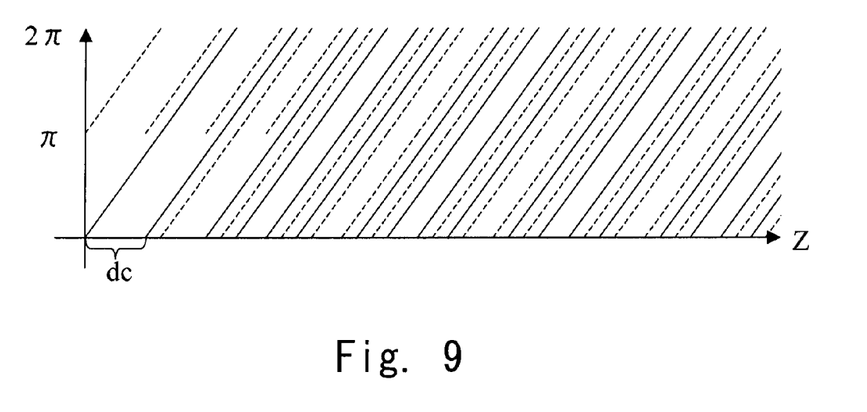
FIG. 9 is a schematic diagram showing the loci of direct data and complementary data for a plurality of cycles.

FIG. 9 is a schematic diagram showing the loci of direct data and complementary data for a plurality of cycles. As indicated in FIG. 9, distances between each acquisition loci are ¼ dc or ½ dc, appearing in a regular manner.

If a helical scan is executed using ±df/8 as the flying focal spots ±σ adapted to the z-FFS method, with neighboring two data acquisition loci distance of ¼ dc, one locus of flying focal spot +σ (+df/8) and the other locus of flying focal spot −σ (−df/8) overlap each other. Therefore, when complementary data is also used, a control that is different from when only direct data is used is needed.

Next, an X-ray CT apparatus 1 of the first modified embodiment that enables high-density data acquisitions when a helical scan is executed is described.

Figure 10:
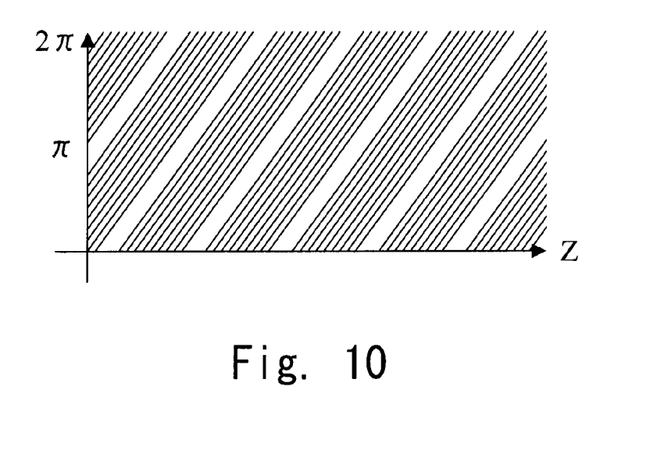
FIG. 10 is a schematic diagram showing the loci of acquisition data of helical scans using the z-FFS method adapting the flying focal spot of a first modified embodiment.

FIG. 10 is a schematic diagram showing the loci of acquisition data of helical scans using the z-FFS method adapting the flying focal spots of the first modified embodiment. In FIG. 10, solid lines indicate all of the data acquisition loci. In FIG. 10, direct data and complementary data are not distinguished. FIG. 10 shows the data acquisition loci in the case that the flying focal spots ±y are ±df/16. Such a flying focal spot setting causes the data acquisition loci to not overlap each other and to have a higher density compared to the case of not using the z-FFS method.

In the X-ray CT apparatus of the first modified embodiment, flying focal spots ±σ are set to ±df/16 so that the loci do not overlap and have a higher density than when flying focal spots ±σ are ±df/4 or ±df/8.

In addition, the first modified embodiment should not be limited to the case in which the helical pitch is 2.5 dc, as explained above. If the helical pitch is (an integer n+0.5) dc (e.g., 1.5 dc, 3.5 dc, etc.), there can exist regions where the distances between each acquisition loci is ¼ dc. In such cases, setting the flying focal spot to ±σ±df/16 causes the loci to not overlap each other as when the helical pitch is 2.5 dc.

Furthermore, the first modified embodiment is not limited to the case in which the flying focal spots ±σ are ±df/16, as explained above. The flying focal spots ±σ may be set to other values so that the loci do not overlap each other. Therefore, the flying focal spots ±σ may be at least ±σ<±df/8.

Second Modified Embodiment

Next, a second modified embodiment is described. The case in which the helical pitch is 2.5 dc is described above. However, in the second modified embodiment, the helical pitch is 3 dc and complementary data is also used.

Figure 11:
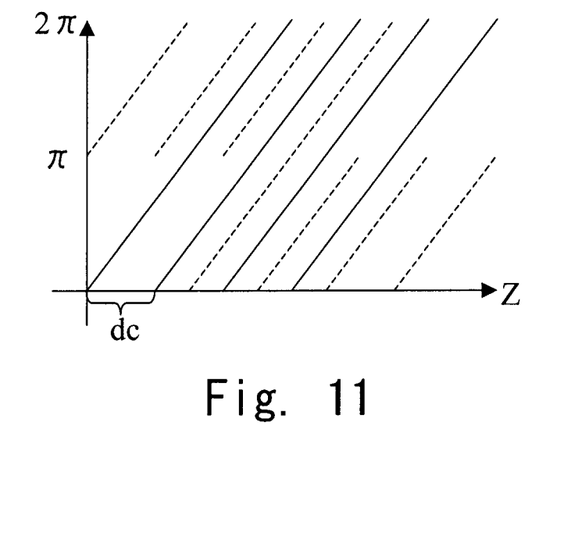
FIG. 11 is a schematic diagram showing the loci of acquisition data including direct data and complementary data of the 4-row X-ray detector elements for one cycle using a 3 dc helical pitch.

First of all, data loci when the helical data pitch is 3 dc is explained. FIG. 11 is a schematic diagram showing the loci of acquisition data of the 4-row X-ray detector elements for one cycle using a 3 dc helical pitch. Solid lines indicate direct data and dashed lines indicate complementary data. Complementary data positions are shifted by π along the rotational direction from the direct data. When the scan is repeated, another 3 dc shifted acquisition loci shown in FIG. 11 is superimposed on the acquisition loci.

Figure 12:
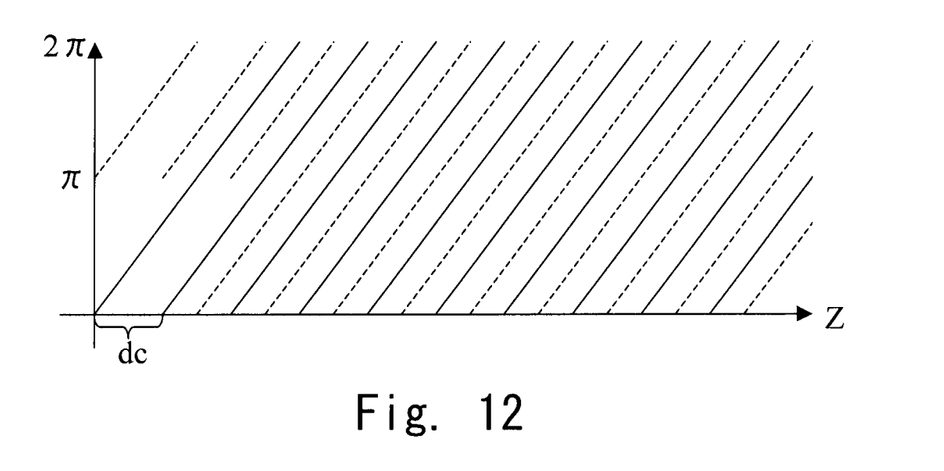
FIG. 12 is a schematic diagram showing the loci of direct data and complementary data using a 3 dc helical pitch for a plurality of cycles.

FIG. 12 is a schematic diagram showing the loci of acquisition data using a 3 dc helical pitch for a plurality of cycles. In the second modified example, some loci overlap. However, assuming that the overlapped loci are one locus, as indicated in FIG. 12, the distance between each acquisition loci is ½ dc.

If a helical scan is executed using ±df/4 as the flying focal spots ±σ adapted to the z-FFS method, with regard to neighboring two data acquisition loci distance of ½ dc, one locus of flying focal spot +σ(+df/4) and the other locus of flying focal spot −σ (−df/4) overlap each other.

Next, an X-ray CT apparatus 1 of the second modified embodiment that enables high-density data acquisitions when a helical scan is executed is described. Since a distance between neighboring two data acquisition loci is ½ dc, a same manner as the case when using a helical pitch of 2.5 dc and not using complementary data can be adapted. Therefore, in the second modified embodiment, the flying focal spots ±σ may be ±df/8.

In the X-ray CT apparatus of the second modified embodiment, the flying focal spots ±σ are set to ±df/8 so that the loci do not overlap and have a higher density than when the flying focal spots ±σ are ±df/4 is enabled. This results in a faster helical scan because the helical pitch is 3 dc, which is larger than 2.5 dc.

In addition, the second modified embodiment should not be limited to the case in which the helical pitch is 3 dc, as explained above. If the helical pitch is 2n−1 dc, wherein n is an integer, (e.g., 1 dc, 5 dc, etc.), there can exist regions where the distance between each acquisition loci is ½ dc. In such cases, setting the flying focal spots ±σ to ±df/8 causes the loci to not overlap each other, as with the case of a helical pitch of 3 dc.

Furthermore, the second modified embodiment should not be limited to the case in which the flying focal spots ±σ are ±df/8, as explained above. The flying focal spots ±σ may be set to other values so that the loci do not overlap each other. Therefore, the flying focal spots ±σ may be at least ±σ<±df/4.

Meanwhile, in each of the above-mentioned embodiments, the fluctuation should not be limited to the case in which the flying focal spot moves symmetrically toward the standard position of the focus. If the amplitude of the fluctuation is substantially the same as in the above-mentioned embodiments, asymmetric fluctuation of the focal point also causes the same effect. For example, instead of ±df/8 defined as the flying focal spot ±σ, df/4 may be defined as the amplitude of the fluctuation of the flying focal spot.

While certain embodiments have been described, these embodiments have been presented by way of example only, and are not intended to limit the scope of the inventions. Indeed, the novel methods and systems described herein may be embodied in a variety of other forms. Furthermore, various omissions, substitutions, and changes in the form of the methods and systems described herein may be made without departing from the sprit of the inventions. The accompanying claims and their equivalents are intended to cover such forms or modifications as would fall within the scope and spirit of the inventions.

What is claimed is:

1. An apparatus for X-ray CT imaging, comprising:
   an X-ray irradiation unit configured to irradiate an X-ray toward a subject;
   an X-ray detector having a plurality of X-ray detection elements along a channel direction and a row direction;
   a couch on which the subject can be arranged;
   a rotation unit on which the X-ray irradiation unit is disposed and rotates around the couch;
   a controller configured to execute a helical scan while fluctuating an X-ray focal spot along a body axis direction of the subject by controlling the X-ray irradiation unit; and
   an image processing unit configured to generate a reconstructed image based on data acquired by the helical scan, wherein
   the controller is further configured to set a magnitude of fluctuation of the X-ray focal spot based on a distance between the X-ray focal spot and a rotation center axis, a distance between the X-ray focal spot and a center of the X-ray detector, and a pitch of the plurality of X-ray detection elements.

2. The apparatus for X-ray CT imaging of claim 1, wherein the controller is further configured to set the magnitude of fluctuation D to be $$D < \frac{d \cdot SOD}{2 \cdot (SDD - SOD)},$$

wherein SOD is defined as the distance between the X-ray focal spot and the rotation center axis of the X-ray irradiation unit and the X-ray detector, SDD is defined as the distance between the X-ray focal spot and the center of the X-ray detector, and d is defined as the pitch of the plurality of X-ray detection elements.

3. The apparatus for X-ray CT imaging of claim 2, wherein the controller is further configured to control the helical scan so that a helical pitch is substantially equal to (n +0.5) dc, wherein n is an integer and dc is a projected pitch, which is a projected length of the pitch of the plurality of X-ray detection elements at a rotation center axis of the X-ray irradiation unit and the X-ray detector.

4. The apparatus for X-ray CT imaging of claim 3, wherein the controller is further configured to control the helical scan so that the helical pitch is substantially equal to 2.5 dc.

5. The apparatus for X-ray CT imaging of claim 3, wherein
the image processing unit is further configured to generate the reconstructed image based on direct data acquired by the helical scan; and
the controller is further configured to set the magnitude of fluctuation D to be $$D = \frac{d \cdot SOD}{4 \cdot (SDD - SOD)}.$$

6. The apparatus for X-ray CT imaging of claim 3, wherein
the image processing unit is further configured to generate the reconstructed image based on direct data and complementary data acquired by the helical scan; and
the controller is further configured to set the magnitude of fluctuation D to be $$D = \frac{d \cdot SOD}{8 \cdot (SDD - SOD)}.$$

7. The apparatus for X-ray CT imaging of claim 2, wherein the controller is further configured to control the helical scan so that a helical pitch is substantially equal to (2n +1) dc, wherein n is an integer and dc is a projected pitch, which is a projected length of the pitch of the plurality of X-ray detection elements at a rotation center axis of the X-ray irradiation unit and the X-ray detector.

8. The apparatus for X-ray CT imaging of claim 7, wherein
the image processing unit is further configured to generate the reconstructed image based on direct data and complementary data acquired by the helical scan; and
the controller is further configured to set the magnitude of fluctuation D to be $$D = \frac{d \cdot SOD}{4 \cdot (SDD - SOD)}.$$

9. The apparatus for X-ray CT imaging of claim 7, wherein the controller is further configured to control the helical scan so that the helical pitch is substantially equal to 3 dc.

10. The apparatus for X-ray CT imaging of claim 1, wherein the controller is further configured to set the magnitude of fluctuation D to be $$D < \frac{d \cdot SOD}{4 \cdot (SDD - SOD)},$$

wherein SOD is defined as the distance between the X-ray focal spot and the rotation center axis of the X-ray irradiation unit and the X-ray detector, SDD is defined as the distance between the X-ray focal spot and the center of the X-ray detector, and d is defined as the pitch of the plurality of X-ray detection elements.

11. A method for X-ray CT imaging, comprising:
irradiating an X-ray toward a subject arranged on a couch, using an X-ray irradiation unit;
detecting the X-ray using an X-ray detector having a plurality of X-ray detection elements along a channel direction and a row direction;
rotating a rotation unit, on which the X-ray irradiation unit is disposed, around the couch;
executing a helical scan while fluctuating an X-ray focal spot along a body axis direction of the subject by controlling the X-ray irradiation unit;
generating a reconstructed image based on data acquired by the helical scan; and
setting a magnitude of fluctuation of the X-ray focal spot based on a distance between the X-ray focal spot and a rotation center axis, a distance between the X-ray focal spot and a center of the X-ray detector, and a pitch of the plurality of X-ray detection elements.

12. The method for X-ray CT imaging of claim 11, wherein the setting step comprises setting the magnitude of fluctuation D to be $$D < \frac{d \cdot SOD}{2 \cdot (SDD - SOD)},$$

wherein SOD is defined as the distance between the X-ray focal spot and the rotation center axis of the X-ray irradiation unit and the X-ray detector, SDD is defined as the distance between the X-ray focal spot and the center of the X-ray detector, and d is defined as the pitch of the plurality of X-ray detection elements.

13. The method for X-ray CT imaging of claim 12, wherein the executing step further comprises controlling the helical scan so that a helical pitch is substantially equal to (n +0.5) dc, wherein n is an integer and dc is a projected pitch, which is a projected length of the pitch of the plurality of X-ray detection elements at a rotation center axis of the X-ray irradiation unit and the X-ray detector.

14. The method for X-ray CT imaging of claim 13, wherein the helical pitch is substantially equal to 2.5 dc.

15. The method for X-ray CT imaging of claim 13, wherein
the generating step comprises generating the reconstructed image based on direct data acquired by the helical scan; and
the setting step comprises setting the magnitude of fluctuation D to be $$D = \frac{d \cdot SOD}{4 \cdot (SDD - SOD)}.$$

16. The method for X-ray CT imaging of claim 13, wherein
the generating step comprises generating the reconstructed image based on direct data and complementary data acquired by the helical scan; and the setting step comprises setting the magnitude of fluctuation D to be $$D = \frac{d \cdot SOD}{8 \cdot (SDD - SOD)}.$$

17. The method for X-ray CT imaging of claim 12, wherein the executing step further comprises controlling the helical scan so that a helical pitch is substantially equal to (2n +1) dc, wherein n is an integer and de is a projected pitch, which is a projected length of the pitch of the plurality of X-ray detection elements at a rotation center axis of the X-ray irradiation unit and the X-ray detector.

18. The method for X-ray CT imaging of claim 17, wherein
the generating step comprises generating the reconstructed image based on direct data and complementary data acquired by the helical scan; and
the setting step comprises setting the magnitude of fluctuation D to be $$D = \frac{d \cdot SOD}{4 \cdot (SDD - SOD)}.$$

19. The method for X-ray CT imaging of claim 17, wherein the helical pitch is substantially equal to 3 dc.

20. The method for X-ray CT imaging of claim 11, wherein the setting step comprises setting the magnitude of fluctuation D to be $$D < \frac{d \cdot SOD}{4 \cdot (SDD - SOD)},$$

wherein SOD is defined as the distance between the X-ray focal spot and the rotation center axis of the X-ray irradiation unit and the X-ray detector, SDD is defined as the distance between the X-ray focal spot and the center of X-ray detector, and d is defined as the pitch of the plurality of X-ray detection elements.

* * * * *